US012178803B2

(12) United States Patent
Johnson et al.

(10) Patent No.: US 12,178,803 B2
(45) Date of Patent: Dec. 31, 2024

(54) CD47 BLOCKADE WITH PARP INHIBITION FOR DISEASE TREATMENT

(71) Applicant: TRILLIUM THERAPEUTICS ULC, Mississauga (CA)

(72) Inventors: Lisa Danae Schultz Johnson, Etobicoke (CA); Lei Cui, Newton, MA (US)

(73) Assignee: Pfizer Inc., New York, NY (US)

( * ) Notice: Subject to any disclaimer, the term of this patent is extended or adjusted under 35 U.S.C. 154(b) by 831 days.

(21) Appl. No.: 17/272,413

(22) PCT Filed: Aug. 29, 2019

(86) PCT No.: PCT/CA2019/051195
§ 371 (c)(1),
(2) Date: Mar. 1, 2021

(87) PCT Pub. No.: WO2020/047651
PCT Pub. Date: Mar. 12, 2020

(65) Prior Publication Data
US 2021/0315864 A1 Oct. 14, 2021

Related U.S. Application Data

(60) Provisional application No. 62/726,497, filed on Sep. 4, 2018.

(51) Int. Cl.
| | | |
|---|---|---|
| *A61K 31/4184* | (2006.01) | |
| *A61K 31/166* | (2006.01) | |
| *A61K 31/454* | (2006.01) | |
| *A61K 31/5025* | (2006.01) | |
| *A61K 41/00* | (2020.01) | |
| *A61P 35/00* | (2006.01) | |
| *C07K 14/705* | (2006.01) | |

(52) U.S. Cl.
CPC ........ *A61K 31/4184* (2013.01); *A61K 31/166* (2013.01); *A61K 31/454* (2013.01); *A61K 31/5025* (2013.01); *A61K 41/0038* (2013.01); *A61P 35/00* (2018.01); *C07K 14/70503* (2013.01)

(58) Field of Classification Search
CPC .............. A61K 31/4184; A61K 31/166; A61K 31/454; A61K 31/5025; A61K 41/0038; A61P 35/00; C07K 14/70503
See application file for complete search history.

(56) References Cited

U.S. PATENT DOCUMENTS

| | | | |
|---|---|---|---|
| 6,277,375 | B1 | 8/2001 | Ward |
| 6,913,894 | B2 | 7/2005 | Buhring et al. |
| 8,562,997 | B2 | 10/2013 | Jaiswal et al. |
| 9,969,789 | B2 * | 5/2018 | Uger ........................ A61P 35/00 |
| 10,906,954 | B2 * | 2/2021 | Uger ................ C07K 14/70503 |
| 11,622,961 | B2 * | 4/2023 | Sun ..................... A61K 31/4439 514/342 |
| 11,771,764 | B2 * | 10/2023 | Cui .......................... A61P 35/02 600/1 |
| 2015/0329616 | A1 * | 11/2015 | Uger ....................... A61P 35/00 435/328 |
| 2021/0206829 | A1 * | 7/2021 | Uger ....................... A61P 35/00 |

FOREIGN PATENT DOCUMENTS

| | | | |
|---|---|---|---|
| WO | WO-2010/070047 A1 | 6/2010 | |
| WO | WO-2010/083253 A2 | 7/2010 | |
| WO | WO-2013/056352 A1 | 4/2013 | |
| WO | WO-2013109752 A1 * | 7/2013 | ............. A61P 35/00 |
| WO | WO-2014/094122 A1 | 6/2014 | |
| WO | WO-2014/123580 A1 | 8/2014 | |
| WO | WO-2014/160183 A1 | 10/2014 | |
| WO | WO-2016/022971 A1 | 2/2016 | |
| WO | WO-2016/024021 A1 | 2/2016 | |
| WO | WO-2018/107058 A1 | 6/2018 | |
| WO | WO-2018/213732 A1 | 11/2018 | |
| WO | WO-2018236904 A1 * | 12/2018 | ........... A61K 31/495 |
| WO | WO-2019/079548 A1 | 4/2019 | |
| WO | WO-2019/084692 A1 | 5/2019 | |

OTHER PUBLICATIONS

Ngo et al. "Antibody Therapy Targeting CD47 and CD271 Effectively Suppresses Melanoma Metastasis in Patient-Derived Xenografts", 2016, Cell Reports, 16, pp. 1-16 (Year: 2016).*
Baskar et al. "Cancer and Radiation Therapy: Current Advances and Future Directions", 2012, International Journal of Medical Sciences, 9, pp. 193-199 (Year: 2012).*
Malyuchenko et al., "PARP-1 Inhibitors: Antitumor Drug Design", 2015, Acta Naturae, 3, pp. 27-37 (Year: 2015).*
Benafif et al., An update on PARP inhibitors for the treatment of cancer, Onco Targets Ther., 8:519-28 (Feb. 2015).
Cui et al., P362 TTI-621 (SIRPaFc), an immune checkpoint inhibitor blocking the CD47 "do not eat" signal, enhances the anti-tumor effect of radiation and targeted therapy in ovarian cancer models, Abstract P362, Journal for ImmunoTherapy of Cancer, 6(Suppl 1):114, 33rd Annual Meeting & Pre-Conference Programs of the Society for Immunotherapy of Cancer (SITC 2018) (2018).
Dréan et al., PARP inhibitor combination therapy, Crit. Rev. Oncol. Hematol., 108:73-85 (Dec. 2016).
International Application No. PCT/CA2019/051195, International Search Report and Written Opinion, mailed Nov. 15, 2019.

(Continued)

*Primary Examiner* — Jeffrey H Murray
*Assistant Examiner* — Madeline E Braun
(74) *Attorney, Agent, or Firm* — Corey Williams

(57) ABSTRACT

CD47+ disease cells such as cancer cells are treated using a combination of CD47 blocking agent and poly-(ADP-ribose) polymerase (PARP) inhibitor. The CD47 blocking agent can be SIRPαFc and the PARP inhibitor niraparib. The anti-cancer effect of niraparib is enhanced in the presence of SIRPαFc. Specific combinations include SIRPαFc forms that comprise an Fc that is either IgG1 or preferably IgG4 isotype. These combinations are useful particularly to treat solid tumours and blood cancers including lymphomas, leukemias and myelomas.

Figure 1:
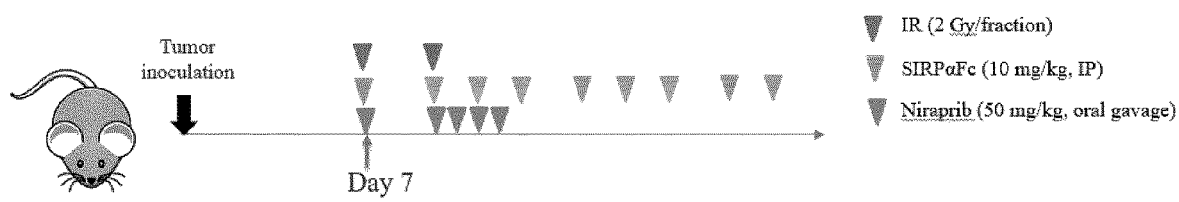

13 Claims, 1 Drawing Sheet
Specification includes a Sequence Listing.

(56) References Cited

OTHER PUBLICATIONS

Lesueur et al., Poly-(ADP-ribose)-polymerase inhibitors as radiosensitizers: a systematic review of pre-clinical and clinical human studies, Oncotarget, 8(40):69105-24 (Jul. 2017).
Maxhimer et al., Radioprotection in normal tissue and delayed tumor growth by blockade of CD47 signaling, Sci. Transl. Med., 1(3):3ra7 (Oct. 2009).
Petrova et al., TTI-621 (SIRPaFc): A CD47-Blocking Innate Immune Checkpoint Inhibitor with Broad Antitumor Activity and Minimal Erythrocyte Binding, Clin. Cancer Res., 23(4):1068-79 (Feb. 2017).
Weiskopf, Kipp, Cancer immunotherapy targeting the CD47/SIRPx axis, European Journal of Cancer, vol. 76, p. 100-109, 2017.
Ricks, Tiffany K., et al., Successes and challenges of PARP inhibitors in cancer therapy, Frontiers In Oncology, vol. 5, Article 222, p. 1-5, 2015.
"PARP inhibitors as molecularly targeted drugs", Vitamin, 2013 vol. 87, No. 8, p. 454-457.

\* cited by examiner

SEQUENCE LISTING

<160> NUMBER OF SEQ ID NOS: 10

<210> SEQ ID NO 1
<211> LENGTH: 106
<212> TYPE: PRT
<213> ORGANISM: Homo sapiens

<400> SEQUENCE: 1

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
                20                  25                  30

Gly Pro Ile Gln Trp Phe Arg Gly Ala Gly Pro Ala Arg Glu Leu Ile
            35                  40                  45

Tyr Asn Gln Lys Glu Gly His Phe Pro Arg Val Thr Thr Val Ser Glu
        50                  55                  60

Ser Thr Lys Arg Glu Asn Met Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Thr Glu Phe Lys Ser Gly Ala
                100                 105

<210> SEQ ID NO 2
<211> LENGTH: 227
<212> TYPE: PRT
<213> ORGANISM: Homo sapiens

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 345
<212> TYPE: PRT
<213> ORGANISM: Homo sapiens

<400> SEQUENCE: 3

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys

```
                210                 215                 220
Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
                260                 265                 270

Ser Asp Ile Ala Val Glu Trp Glu Ser Asn Gly Gln Pro Glu Asn Asn
                275                 280                 285

Tyr Lys Thr Thr Pro Pro Val Leu Asp Ser Asp Gly Ser Phe Phe Leu
                290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
                340                 345
```

<210> SEQ ID NO 4
<211> LENGTH: 11
<212> TYPE: PRT
<213> ORGANISM: Artificial Sequence
<220> FEATURE:
<223> OTHER INFORMATION: Artificial Linker

<400> SEQUENCE: 4

```
Gly Thr Glu Leu Ser Val Arg Ala Lys Pro Ser
1               5                   10
```

<210> SEQ ID NO 5
<211> LENGTH: 118
<212> TYPE: PRT
<213> ORGANISM: Homo sapiens

<400> SEQUENCE: 5

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Lys Glu Gly His Phe Pro Arg Val Thr Thr Val Ser
                50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
                115
```

<210> SEQ ID NO 6
<211> LENGTH: 229
<212> TYPE: PRT
<213> ORGANISM: Homo sapiens

<400> SEQUENCE: 6

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140
```

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
        180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 8
<211> LENGTH: 345
<212> TYPE: PRT
<213> ORGANISM: Homo sapiens

<400> SEQUENCE: 8

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
            165                 170                 175

Val Asp Gly Val Glu Val His Asn Ala Lys Thr Lys Pro Arg Glu Glu
        180                 185                 190

Gln Tyr Asn Ser Thr Tyr Arg Val Val Ser Val Leu Thr Val Leu His
    195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn

```
            275                 280                 285
Tyr Lys Thr Thr Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
                340                 345

<210> SEQ ID NO 9
<211> LENGTH: 347
<212> TYPE: PRT
<213> ORGANISM: Homo sapiens

<400> SEQUENCE: 9

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser Glu Ser Lys Tyr Gly Pro Pro Cys Pro Pro
            115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Asn Ser Thr Tyr Arg Val Val Ser Val Leu Thr Val
            195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
    290                 295                 300
```

```
Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 10
<211> LENGTH: 5
<212> TYPE: PRT
<213> ORGANISM: Artificial Sequence
<220> FEATURE:
<223> OTHER INFORMATION: Artificial Linker

<400> SEQUENCE: 10

Gly Gly Gly Gly Ser
1               5
```

CD47 BLOCKADE WITH PARP INHIBITION FOR DISEASE TREATMENT

CROSS-REFERENCE TO RELATED APPLICATION

This application is a National Stage application of International Application No. PCT/CA2019/051195, filed Aug. 29, 2019, which claims the benefit of U.S. Provisional Patent Application No. 62/726,497 filed on Sep. 4, 2018, which is incorporated herein by reference in its entirety.

INCORPORATION BY REFERENCE OF MATERIAL SUBMITTED ELECTRONICALLY

The Sequence Listing, which is a part of the present disclosure, is submitted with the specification as a text file named "56488_Seqlisting.txt", which was created on Feb. 26, 2021, and is 17,806 bytes in size. The subject matter of the Sequence Listing is incorporated herein in its entirety by reference.

FIELD

This invention relates to methods of using a drug that blocks the CD47/SIRPα interaction. More particularly, the invention relates to methods and means that, in combination, are useful for improving cancer therapy.

BACKGROUND

CD47 is an immune checkpoint that binds to signal regulatory protein alpha (SIRPα) and delivers a "do not eat" signal to suppress macrophage phagocytosis. Tumor cells frequently overexpress CD47 to evade macrophage-mediated destruction. Trillium's WO2014/094122 describes a protein drug that inhibits the interaction between CD47 and SIRPα. This CD47 blocking agent is a form of human SIRPα that incorporates a particular region of its extracellular domain linked with a particularly useful form of an IgG1-based Fc region. A related form of SIRPα having an IgG4-based Fc region is also described. In these forms, SIRPαFc shows dramatic effects on the viability of cancer cells that present with a CD47+ phenotype. The effect is seen particularly on acute myelogenous leukemia (AML) cells, and on many other types of cancer. A soluble form of SIRP having significantly altered primary structure and enhanced CD47 binding affinity is described in WO2013/109752.

Other CD47 blocking agents have been described in the literature and these include various CD47 antibodies (see for instance Stanford's U.S. Pat. No. 8,562,997, and InhibRx' WO2014/123580), each comprising different antigen binding sites but having, in common, the ability to compete with endogenous SIRPα for binding to CD47, thereby to allow interaction with macrophages and, ultimately, to increase the rate of CD47+ cancer cell depletion. These CD47 antibodies have activities in vivo that are quite different from those intrinsic to SIRPα-based drugs. The latter, for instance, display negligible binding to red blood cells whereas the opposite property in CD47 antibodies creates a need for strategies that accommodate the drug "sink" that follows administration.

Still other agents are proposed for use in blocking the CD47/SIRPα axis. These include CD47Fc proteins (see Viral Logic's WO2010/083253), and SIRPα antibodies as described in UHN's WO2013/056352, Stanford's WO2016/022971, Eberhard's U.S. Pat. No. 6,913,894, and elsewhere.

The CD47 blockade approach in anti-cancer drug development shows great promise. It would be useful to provide methods and means for improving the effect of these drugs, and in particular for improving the effect of the CD47 blocking agents, especially those that incorporate SIRPα.

SUMMARY

It has now been found that the anti-cancer effect of a CD47 blocking agent is improved when combined with an agent that inhibits activity of the enzyme known as poly (ADP-ribose) polymerase, i.e., "PARP". In embodiments, the CD47 blocking agent is a SIRPα-Fc polypeptide. In other embodiments, the PARP inhibitor is an inhibitor of PARP-1. The benefit arising from the treatment combination of PARP inhibitor and CD47 blocking agent is particularly surprising in that PARP inhibition is usually enhanced by DNA damaging agents, and this DNA damaging activity has not been reported for CD47 blocking agents.

In one aspect, there is provided a method for treating a subject presenting with CD47+ disease cells, comprising administering to the subject a CD47 blocking agent and a PARP inhibiting agent. In a related aspect, the present invention provides for the use of a SIRPαFc fusion protein in combination with a PARP inhibitor, for the treatment of a subject presenting with CD47+ disease cells including CD47+ cancer cells and tumours. In another aspect, there is provided a combination comprising a SIRPαFc fusion protein and a PARP inhibitor for use in the treatment of a subject presenting with CD47+ disease cells including CD47+ cancer cells and tumours.

There is also provided, in another aspect, a pharmaceutical combination comprising a CD47 blocking agent, such as a SIRPαFc polypeptide, and a PARP inhibiting agent together with instructions teaching their use in the treatment method herein described. In a related aspect there is provided an article of manufacture, comprising at least one of the two agents and instructions for the use thereof in combination with the other of the two agents in the treatment of a subject presenting with CD47+ disease cells such as cancer. In embodiments, there is provided a kit comprising at least one or both of the two agents, packaged separately for use in combination with the present method.

It has also been found that treatment with the combination of a CD47 blocking agent and a PARP inhibitor can be enhanced still further when that treatment is supplemented by radiotherapy. One demonstrated benefit of this triple treatment combination is enhanced survival. Thus, in aspects, there is provided a triple combination therapy that makes use of radiotherapy, a PARP inhibitor and a CD47 blocking agent for the treatment of disease cells.

In other aspects there is provided an article of manufacture such as in the form of a kit containing material useful for the treatment of the disease cells and tumours described herein is provided.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF REFERENCE TO THE DRAWINGS

FIG. 1 shows the drug combination study design and the dosing regimen. $5\times10^6$ luciferase expressing tumor cells suspended in PBS were injected intraperitoneally into NOD/SCID mice in a final volume of 0.2 mL on day 0. The mice were imaged by BLI, and randomized into different treatment groups based on their BLI imaging on Day 6. Mice were treated with vehicle control, IR, niraparib, SIRPαFc, or their combination starting from day 7 post tumor inoculation.

Figure 2:
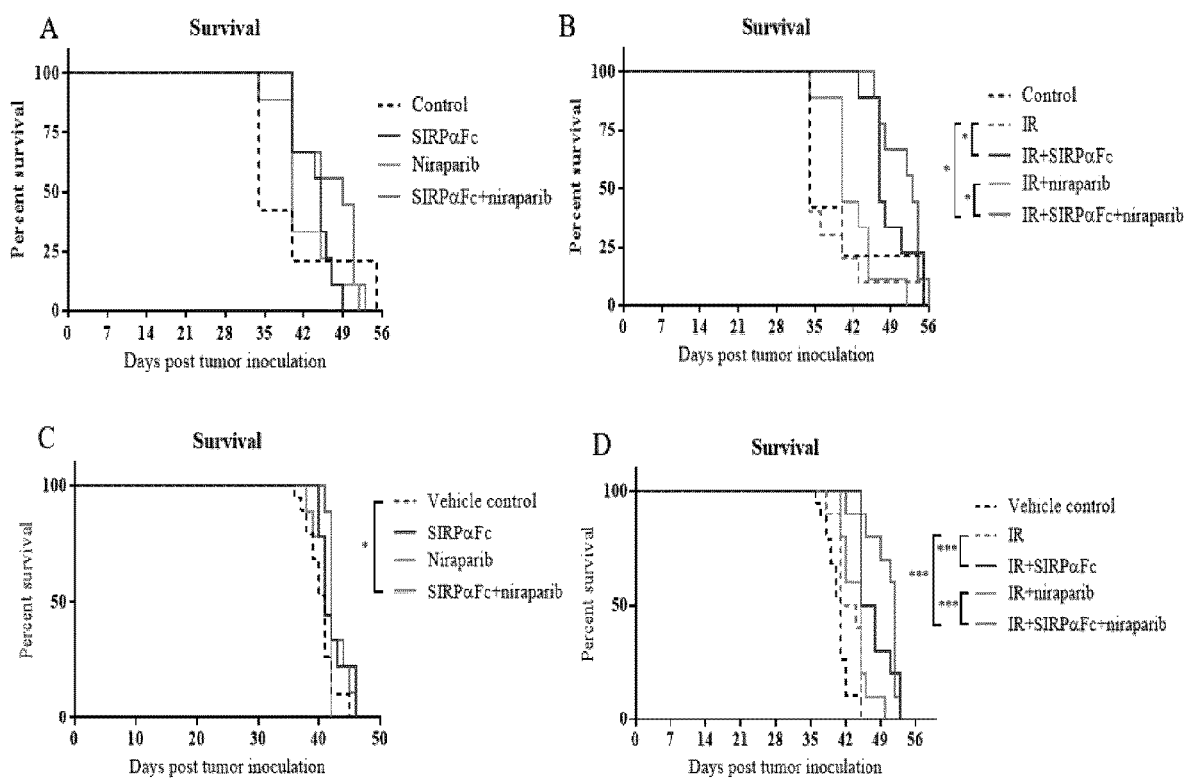

FIG. 2 provides survival curves (Kaplan-Meier plots) of animals following treatment, animals were treated with vehicle control, SIRPαFc, niraparib (a PARPi), irradiation (IR), either alone, or in combination 7 days following tumor inoculation. Animal survival following treatment. (A) & (B) Survival of animals bearing intraperitoneal tumors of BRCA competent SKOV-3. (C) & (D) Survival of animals bearing intraperitoneal tumors of BRCA knock-down SKOV-3.

DETAILED DESCRIPTION AND PREFERRED EMBODIMENTS

The present invention provides an improved method for treating a subject presenting with CD47+ disease cells such as cancer cells and tumours that have a CD47+ phenotype. In this method, subjects receive a combination of a CD47 blocking agent such as SIRPαFc, and an inhibitor of the enzyme, poly-(ADP ribose) polymerase, designated PARP. The effect of this treatment on CD47+ disease cells is improved relative to the effect of treatment with either agent alone. While PARP inhibitors are known to be able to enhance the efficacy of DNA damaging therapeutics such as radiotherapy via elevated cytotoxic effect on tumor cells, the synergistic effect of niraparib (a PARP inhibitor) and SIRPαFc described here stems from tumor cell kill by niraparib and immune modulation by SIRPαFc. This combination effect is not expected when a PARP inhibitor is used with an agent other than another DNA damaging agent.

The term "CD47+" is used herein with reference to the phenotype of cells targeted for treatment with a CD47 blocking agent. Cells that are CD47+ can be identified by flow cytometry using CD47 antibody as the affinity ligand. Labeled CD47 antibodies are available commercially for this use (for example, clone B6H12 is available from Santa Cruz Biotechnology). The cells examined for CD47 phenotype can be standard tumour biopsy samples including particularly liquid and tissue samples taken from the subject suspected of harbouring CD47+ cancer cells. CD47 disease cells of particular interest as targets for therapy with the present combination are those that "over-express" CD47. These CD47+ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry or by immunostaining or by gene expression analysis or the like, to be greater than the level measurable on a counterpart cell having a CD47 phenotype that is normal for that cell type.

As used herein, a "CD47 blocking agent" can be any drug or agent that interferes with and dampens or blocks signal transmission that results when CD47 interacts with macrophage-presented SIRPα. The CD47 blocking agent is an agent that inhibits CD47 interaction with SIRPα. The CD47 blocking agent is preferably an agent that binds CD47 and blocks its interaction with SIRPα. The CD47 blocking agent can be an antibody or antibody-based antagonist of the CD47/SIRPα signaling axis, such as an antibody that binds CD47 and blocks interaction of CD47 with SIRPα. Desirably, but not essentially, the CD47 blocking agent comprises a constant region, i.e., an Fc region, that can be bound by macrophages that are activated to destroy cells to which the CD47 blocking agent is bound, such as cancer cells. The CD47 blocking agent Fc region preferably has effector function, and is derived preferably from either IgG1 or IgG4 including IgG4(S228P). In the alternative, the Fc region can be one that is altered by amino acid substitution to alter effector function, e.g., to an inactive state.

CD47-binding forms of human SIRPα are the preferred CD47 blocking agents for use in the combination herein disclosed. These drugs are based on the extracellular region of human SIRPα. They comprise at least a part of the extracellular region sufficient to confer effective CD47 binding affinity and specificity. So-called "soluble" forms of SIRPα, lacking the membrane anchoring component of SIRPα, are useful and are described in the literature and include those referenced in Novartis' WO 2010/070047, Stanford's WO2013/109752, Merck's WO2016/024021 and Trillium's WO2014/094122.

The SIRPαFc drug used in the present method is a monomeric or homodimeric or heterodimeric form of a single chain polypeptide comprising an Fc region of an antibody and a CD47-binding region of human SIRPα. SIRPα-based drugs of this general type are described in the literature and include those referenced in Novartis' WO 2010/070047, Stanford's WO2013/109752, as well as Trillium's WO2014/094122, and certain variants of SIRPαFc as taught in Merck's WO2016/024021.

In preferred embodiments, the SIRPαFc polypeptide has the properties discussed below. More particularly, the polypeptide suitably comprises a CD47-binding part of human SIRPα protein in a form fused directly, or indirectly, with an antibody constant region, or Fc (fragment crystallisable). Unless otherwise stated, the term "human SIRPα" as used herein refers to a wild type, endogenous, mature form of human SIRPα. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of binding with, and triggering signal transduction through CD47. The present invention is directed most particularly to the drug combinations that include the V2 form of SIRPα.

In the present drug combination, useful CD47 blocking agents are SIRPαFc fusion polypeptides that comprise at least one of the three so-called immunoglobulin (Ig) domains within the extracellular region of human SIRPα. More particularly, the present SIRPαFc polypeptides preferably incorporate residues 32-137 of human SIRPα (a 106-mer), which constitute and define the IgV domain of the V2 form according to current nomenclature. This SIRPα sequence, shown below, is referenced herein as SEQ ID NO:1.

[SEQ ID NO: 1]
EELQVIQPDKSVSVAAGESAILHCTVTSLIPVGPIQWFRGAGPARELIYN

QKEGHFPRVTTVSESTKRENMDFSISISNITPADAGTYYCVKFRKGSPDT

EFKSGA

In a preferred embodiment, the SIRPαFc fusion protein incorporates the IgV domain as defined by SEQ ID NO:1, and additional, flanking residues contiguous within the wild type human SIRPα sequence. This preferred form of the IgV domain, represented by residues 31-148 of the V2 form of human SIRPα, is a 118-mer having SEQ ID NO:5 shown below:

[SEQ ID NO: 5]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS

The Fc region of the SIRPαFc fusion polypeptide preferably does have effector function. Fc refers to "fragment crystallisable" and represents the constant region of an IgG antibody comprised principally of the heavy chain constant region and components within the hinge region. Suitable Fc components thus are those having effector function. An Fc component "having effector function" is an Fc component having at least some effector function, such as at least some contribution to antibody-dependent cellular cytotoxicity or some ability to fix complement. Also, the Fc will at least bind to one or more types of Fc receptor. These properties can be revealed using assays established for this purpose. Functional assays include the standard chromium release assay that detects target cell lysis. By this definition, an Fc region that is wild type IgG1 or IgG4 has effector function, whereas the Fc region of a human IgG4 mutated to eliminate effector function, such as by incorporation of an alteration series that includes Pro233, Val234, Ala235 and deletion of Gly236 (EU), is considered not to have effector function. In a preferred embodiment, the Fc is based on human antibodies of the IgG1 isotype. In an alternative embodiment, the Fc is based on the IgG4 isotype, and includes the Pro$^{228}$Ser variation. The Fc region of these antibodies will be readily identifiable to those skilled in the art. In embodiments, the Fc region includes the lower hinge-CH2-CH3 domains.

In a specific embodiment, the Fc region is based on the amino acid sequence of a human IgG1 set out as P01857 in UniProtKB/Swiss-Prot, residues 104-330, and has the amino acid sequence shown below and referenced herein as SEQ ID NO:2:

[SEQ ID NO: 2]
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK*

Thus, in embodiments, the Fc region has either a wild type or consensus sequence of an IgG1 constant region. In alternative embodiments, the Fc region incorporated in the fusion protein is derived from any IgG1 antibody having a typical effector-active constant region. The sequences of such Fc regions can correspond, for example, with the Fc regions of any of the following IgG1 sequences (all referenced from GenBank), for example: BAG65283 (residues 242-473), BAC04226.1 (residues 247-478), BAC05014.1 (residues 240-471), CAC20454.1 (residues 99-320), BAC05016.1 (residues 238-469), BAC85350.1 (residues 243-474), BAC85529.1 (residues 244-475), and BAC85429.1 (residues (238-469).

In other embodiments, the Fc region has a sequence of a wild type human IgG4 constant region. In alternative embodiments, the Fc region incorporated in the fusion protein is derived from any IgG4 antibody having a constant region with effector activity that is present but, naturally, is less potent than the IgG1 Fc region. The sequences of such Fc regions can correspond, for example, with the Fc regions of any of the following IgG4 sequences: P01861 (residues 99-327) from UniProtKB/Swiss-Prot and CAC20457.1 (residues 99-327) from GenBank.

In a specific embodiment, the Fc region is based on the amino acid sequence of a human IgG4 set out as P01861 in UniProtKB/Swiss-Prot, residues 99-327, and has the amino acid sequence shown below and referenced herein as SEQ ID NO:6:

[SEQ ID NO: 6]
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

In embodiments, the Fc region incorporates one or more alterations, usually not more than about 5 such alterations, including amino acid substitutions that affect certain Fc properties. In one specific and preferred embodiment, the Fc region incorporates an alteration at position 228 (EU numbering), in which the serine at this position is substituted by a proline (S$^{228}$P), thereby to stabilize the disulfide linkage within the Fc dimer. Other alterations within the Fc region can include substitutions that alter glycosylation, such as substitution of Asn$^{297}$ by glycine or alanine; half-life enhancing alterations such as T$^{252}$L, T$^{253}$S, and T$^{256}$F as taught in U.S. 62/777,375, and many others including the 409 position. Particularly useful are those alterations that enhance Fc properties while remaining silent with respect to conformation, e.g., retaining Fc receptor binding.

In a specific embodiment, and in the case where the Fc component is an IgG4 Fc, the Fc incorporates at least the S$^{228}$P mutation, and has the amino acid sequence set out below and referenced herein as SEQ ID NO:7:

[SEQ ID NO: 7]
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

The CD47 blocking agent used in the combination is thus a SIRPαFc fusion protein useful to inhibit binding between human SIRPα and human CD47, thereby to inhibit or reduce transmission of the signal mediated via SIRPα-bound CD47, the fusion protein comprising a human SIRPα component and, fused therewith, an Fc component, wherein the SIRPα component comprises or consists of a single IgV domain of human SIRPα V2 and the Fc component is the constant region of a human IgG, wherein the constant region preferably has effector function.

In one embodiment, the fusion protein comprises a SIRPα component consisting at least of residues 32-137 of the V2 form of wild type human SIRPα, i.e., SEQ ID NO:1. In a preferred embodiment, the SIRPα component consists of residues 31-148 of the V2 form of human SIRPα, i.e., SEQ ID NO:5. In another embodiment, the Fc component is the Fc component of the human IgG1 designated P01857, and in a specific embodiment has the amino acid sequence that incorporates the lower hinge-CH2-CH3 region thereof i.e., SEQ ID NO:2.

In a preferred embodiment, therefore, the present method utilizes a CD47 blocking agent that is a SIRPαFc fusion polypeptide, as both an expressed single chain polypeptide and as a secreted dimeric fusion thereof (homodimer), wherein the fusion protein incorporates a SIRPα component having SEQ ID NO:1 and preferably SEQ ID NO:5 and, fused therewith, an Fc region having effector function and having SEQ ID NO:2. When the SIRPα component is SEQ ID NO:1, this fusion protein comprises SEQ ID NO:3, shown below:

[SEQ ID NO: 3]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK*

When the SIRPα component is SEQ ID NO:5, this fusion protein comprises SEQ ID NO:8, shown below:

[SEQ ID NO: 8]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

In alternative embodiments, the Fc component of the fusion protein is based on an IgG4, and preferably an IgG4 that incorporates the $S^{228}P$ mutation. In the case where the fusion protein incorporates the preferred SIRPα IgV domain of SEQ ID NO:5, the resulting IgG4-based SIRPα-Fc protein has SEQ ID NO:9, shown below:

[SEQ ID NO: 9]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

In a preferred embodiment, the fusion protein comprises, as the SIRPα IgV domain of the fusion protein, a sequence that is SEQ ID NO:5. The preferred SIRPαFc is SEQ ID NO:8.

The SIRPα sequence incorporated within the CD47 blocking agent can be varied, as described in the literature. That is, useful substitutions within SIRPα will typically enhance binding affinity for CD47, and can include one or more of the following: $L^4V/I$, $V^6I/L$, $A^{21}V$, $V^{27}I/L$, $^{131}T/S/F$, $E^{47}V/L$, $K^{53}R$, $E^{54}Q$, $H^{56}P/R$, $S^{66}T/G$, $K^{68}R$, $V^{92}I$, $F^{94}V/L$, $V^{63}I$, and/or $F^{103}V$. Still other substitutions include conservative amino acid substitutions in which an amino acid is replaced by an amino acid from the same group. Also as noted, the SIRPα sequence can also be truncated or extended, so long as CD47 binding affinity is retained.

In the SIRPαFc fusion polypeptide, the SIRPα component and the Fc component are fused, either directly or indirectly, to provide a single chain polypeptide that is ultimately produced as a homodimer in which the single chain polypeptides are coupled through intrachain disulfide bonds formed between the Fc regions of individual single chain SIRPαFc polypeptides. The nature of the fusing region that joins the SIRPα region and the Fc is not critical. The fusion may be direct between the two components, with the SIRP component constituting the N-terminal end of the fusion and the Fc component constituting the C-terminal end. Alternatively, the fusion may be indirect, through a linker comprised of one or more amino acids, desirably genetically encoded amino acids, such as two, three, four, five, six, seven, eight, nine or ten amino acids, or any number of amino acids between 5 and 100 amino acids, such as between 5 and 50, 5 and 30 or 5 and 20 amino acids. A linker may comprise a peptide that is encoded by DNA constituting a restriction site, such as a BamHI, ClaI, EcoRI, HindIII, PstI, SalI and XhoI site and the like.

The linker amino acids typically and desirably will provide some flexibility to allow the Fc and the SIRPα components to adopt their active conformations. Residues that allow for such flexibility typically are Gly, Asn and Ser, so that virtually any combination of these residues (and particularly Gly and Ser) within a linker is likely to provide the desired linking effect. In one example, such a linker is based on the so-called $G_4S$ sequence (Gly-Gly-Gly-Gly-Ser) (SEQ ID NO:10) which may repeat as $(G_4S)_n$ where n is 1, 2, 3 or more, or is based on (Gly)n, (Ser)n, (Ser-Gly)n or (Gly-Ser)n and the like. In another embodiment, the linker is GTELSVRAKPS (SEQ ID NO:4). This sequence constitutes a SIRPα sequence that C-terminally flanks the IgV domain (it being understood that this flanking sequence could be considered either a linker or a different form of the IgV domain when coupled with the IgV minimal sequence described above). It is necessary only that the fusing region or linker permits the components to adopt their active conformations, and this can be achieved by any form of linker useful in the art.

The SIRPαFc fusion is useful as a CD47 blocking agent to inhibit interaction between SIRPα and CD47, thereby to block signalling across this axis. Stimulation of SIRPα on macrophages by CD47 is understood to inhibit macrophage-mediated phagocytosis by deactivating myosin-II and the contractile cytoskeletal activity involved in pulling a target into a macrophage. Activation of this cascade is therefore important for the survival of CD47+ disease cells. Blocking this pathway allows macrophages to engulf and eradicate the CD47+ disease cell population.

The present pharmaceutical combination comprises both a CD47 blocking agent such as a SIRPαFc, and an inhibitor of a poly-(ADP ribose)-polymerase (PARP) enzyme activity. The PARP inhibiting agent (PARPi) can be selected from among the known PARPi and particularly from among those PARPi that are either approved for sale or are in clinical development.

The PARPi will inhibit the activity of a target PARP enzyme, and can therefore be identified using any assay that detects PARP inhibition, e.g., an assay that reveals PARP activity on a given PARP substrate in the presence and absence of the PARPi candidate. The enzyme activity that is assessed can be the enzyme's DNA-binding activity, its C-terminal catalytic activity, its auto-modifying activity and/or its caspase cleavage activity. In embodiments, the PARPi will inhibit the activity of a PARP that is a particular one of the PARP family members, which includes 17 different enzyme species that have been characterized based on sequence homology within the catalytic domain. Of the known members of the PARP super-family in humans, PARP-1, PARP-2, tankyrase1, tankyrase2, and vPARP are thought to have roles in DNA repair but PARP-1 accounts for more than 90% cellular PARP activity and remains the most studied. These enzymes form part of a base excision repair complex that can also be targeted by the PARPi useful herein, for instance to inhibit, disrupt or impair complex formation.

In embodiments, the PARPi is an agent that inhibits the activity of PARP-1. The human form of this PARP-1 species is described in terms of its amino acid sequence and in many other respects in the UniProtKB database as P09874, and the enzyme function is designated as EC:2.4.2.30.

In the present pharmaceutical combination, the PARP inhibiting agent can be any agent, whether biologic or small molecule, that interferes with and disrupts the function of PARP enzyme. The agent could be a PARP-binding agent or antibody, or an inhibitor of PARP gene expression or translation, for instance. Alternatively and preferably, the PARP inhibitor is a small molecule chemical entity that inhibits PARP-1 activity. Because PARP cleaves NAD+ to release nicotinamide, many of these PARPi compounds can have a nicotinamide pharmacophore.

In embodiments, the PARPi used in combination with the CD47 blocking agent, such as a SIRPαFc, is a PARP inhibitor selected from among the group comprising or consisting of: veliparib (ABT888), oliparib (AZ2281, KU59436), iniparib (BSI201/BSI401), rucaparib (AG01 4699), niraparib (Zejula®), pamiparib, talazoparib, MK4827, CEP 9722, BMN672, BMN673, E7016, INO-1001, LT-673, MP 124, NMS-P118 and XAV939.

Structures of some of these compounds are shown below for convenience, and all are revealed in the prior art:

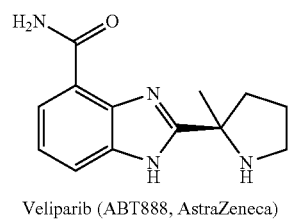

Veliparib (ABT888, AstraZeneca)

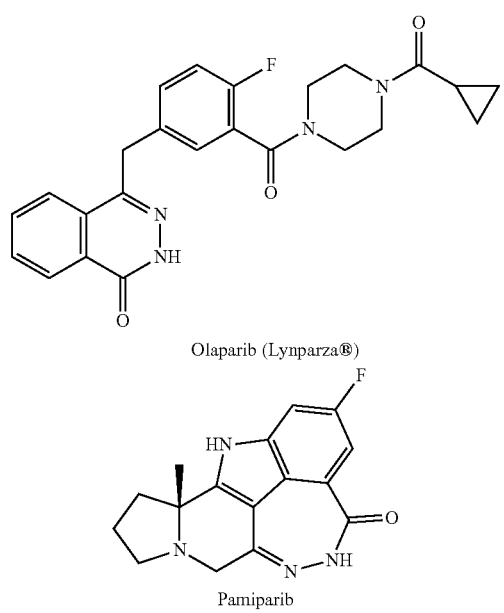

Olaparib (Lynparza®)

Pamiparib

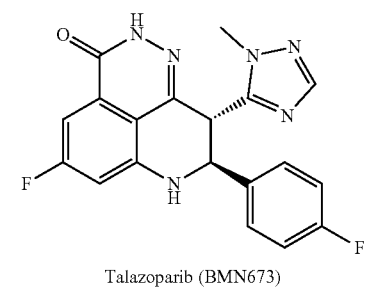

Talazoparib (BMN673)

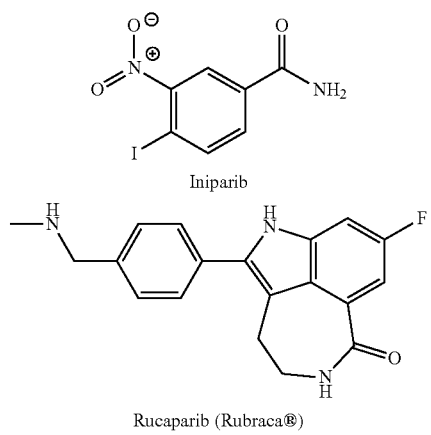

Iniparib

Rucaparib (Rubraca®)

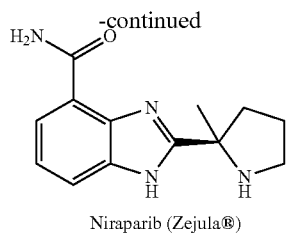

Niraparib (Zejula®)

In a preferred embodiment, the PARP inhibitor is niraparib. Presently, niraparib is approved for use in ovarian cancer treatment without consideration of BRCA status.

The PARP inhibitor can be used in the present combination therapy in the same manner prescribed for its use in monotherapy, including treatment dose, delivery mode, and schedule. Niraparib in particular can be used, for instance, as once daily, orally delivered capsules comprising 100-300 mg of drug (as recommended by FDA). The recommended dose of another PARP inhibitor veliparib was 400 mg bid based on a phase II clinical trial.

More generally, each drug or agent is provided for use in a suitable dosage form comprising a pharmaceutically acceptable carrier, and in a therapeutically effective amount. As used herein, "pharmaceutically acceptable carrier" means any and all solvents, dispersion media, coatings, antibacterial and antifungal agents, isotonic and absorption delaying agents, and the like that are physiologically compatible and useful in the art of protein/antibody formulation, where the CD47 blocking agent is a protein. Otherwise standard agents used in chemical drug formulation can be used to formulate the chosen PARPi. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

As used herein, "effective amount" refers to an amount effective, at dosages and for a particular period of time necessary, to achieve the desired therapeutic result. A therapeutically effective amount of each drug in the combination may vary according to factors such as the disease state, age, sex, and weight of the individual, and the ability of the drug to elicit a desired response in the recipient. A therapeutically effective amount is also one in which any toxic or detrimental effects of the pharmacological agent are outweighed by the therapeutically beneficial effects.

The use of the present pharmaceutical combination can provide an enhanced response that can manifest as an increase in the number of CD47+ disease cells that are killed or impaired by the combined treatment relative to treatment with either agent alone. The response can also manifest as an improvement in the overall burden of CD47+ tumours, or their size, number, growth rate, or distribution in the subject undergoing treatment. This improved efficacy can manifest as a less-than-additive effect, wherein the effect of the combination is greater than the effect of each component alone, but less than the sum of the effects of both components, or it may be an additive effect, wherein the effect of the combination is equivalent to the sum of the effects of the components when used individually, or it may be a greater-than-additive effect, wherein the effect of the combination is greater than the sum of the effects of each component used alone. Greater-than-additive effects may also be described as synergistic. The improved efficacy of the combination can be determined by a number of methods known in the art. Improved efficacy can result in a statistically significant increase in the ability of the combination to inhibit the growth or proliferation or vitality of CD47+ disease cells when compared to the effect of each component alone. In embodiments, the effect is a greater than additive effect. Thus a treatment effective amount or dose of PARPi with SIRPαFc is preferably an amount or dose of the combination that gives an additive or greater than additive effect on the vitality of CD47+ disease cells, or on any other treatment-relevant parameter.

When used in combination with the CD47 blocking agent, the treatment regimen will further consider the selection of drug species to be used in combination, the relative timing of drug administration and the nature of medical indication to be treated. The preferred drug or pharmaceutical combinations are selected from among the following:

1) SIRPαFc having SEQ ID NO:8 or SEQ ID NO:9, and the PARP inhibitor known as niraparib. In a specific embodiment, the combination comprises SIRPαFc having SEQ ID NO:8 and the PARPi niraparib. In another specific embodiment, the combination comprises SIRPαFc having SEQ ID NO:9 and the PARPi niraparib.
2) SIRPαFc having SEQ ID NO:8 or SEQ ID NO:9, and the PARP inhibitor veliparib. In a specific embodiment, the combination comprises SIRPαFc having SEQ ID NO:8 and the PARPi veliparib. In another specific embodiment, the combination comprises SIRPαFc having SEQ ID NO:9 and the PARPi veliparib.
3) SIRPαFc having SEQ ID No. 8 or SEQ ID NO:9 or SEQ ID NO:7, and the PARP inhibitor known as rucaparib. In a specific embodiment, the combination comprises SIRPαFc having SEQ ID NO:8 and the PARPi rucaparib. In another specific embodiment, the combination comprises SIRPαFc having SEQ ID NO:9 and the PARPi rucaparib.
4) SIRPαFc having SEQ ID NO:8 or SEQ ID NO:9 or SEQ ID NO:7, and the PARPi olaparib. In a specific embodiment, the combination comprises SIRPαFc having SEQ ID NO:8 and olaparib. In another specific embodiment, the combination comprises SIRPαFc having SEQ ID NO:9 and olaparib. Each drug included in the combination can be formulated separately for use in combination.

These agents are said to be used "in combination" when the effect of one agent augments the effect of the other, in a recipient of both drugs.

The SIRPαFc and the PARPi may be administered separately or in combination to the subject through any of the routes established for drug delivery. The chosen route and/or mode of administration will vary depending upon the desired results. Preferred routes of administration for fusion proteins such as SIRPαFc are parenteral routes of administration, such as by injection or infusion such as intravenous, intramuscular, intraarterial, intrathecal, intracapsular, intraorbital, intracardiac, intradermal, intraperitoneal, transtracheal, intratumoural, subcutaneous, subcuticular, intraarticular, subcapsular, subarachnoid, intraspinal, epidural and intrasternal. Other routes useful herein particularly for the PARPi are enteral routes such as oral or nasal or pulmonary administration, or by instillation or by a topical, epidermal or mucosal route of administration, for example, intranasally, orally, vaginally, rectally or sublingually, and such routes are established for the approved forms of such PARPi.

The agents in the present combination can be administered sequentially or, essentially at the same time. That is, PARPi can be given before or after administration of SIRPαFc. It is desirable that the agents, or at least their activities, overlap in the recipient. Accordingly, the SIRPαFc can be administered to recipient already treated with PARPi, or vice versa. In a specific embodiment, the CD47 blocking agent, e.g., SIRPαFc, is given after the subject is treated with a PARP inhibitor, such as niraparib. In the alternative, the PARPi and SIRPαFc are administered concomitantly.

Dosing regimens are adjusted to provide the optimum desired response (e.g., a therapeutic response). For example, a single bolus of each drug may be administered, or several divided doses may be administered over time or the dose may be proportionally reduced or increased as indicated by the therapeutic situation. It is especially advantageous to formulate parenteral compositions in unit dosage form for ease of administration and uniformity of dosage. "Unit dosage form" as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The drugs can be formulated in combination, so that the combination can be introduced to the recipient in one administration, e.g., one injection or one infusion bag. In another embodiment, the drugs are formulated separately for separate administration in a combination therapy regimen.

For administration, the dose for each agent will be within the range from about 0.0001 to 100 mg/kg, and more usually 0.01 to 5 mg/kg, of the host body weight. For example dosages can be 0.1 mg/kg body weight, 0.2 mg/kg body weight, 0.3 mg/kg body weight, 1 mg/kg body weight, 3 mg/kg body weight, 5 mg/kg body weight or 10 mg/kg body weight or within the range of 1-10 mg/kg. Unit dosage forms, a drug will comprise from 1-500 mgs of drug, such as 1, 2, 3, 4 5, 10 25, 50, 100, 200, 250, and 500 mgs/dose. The two drugs can be administered in roughly equimolar amounts (+/−10%). An exemplary treatment regimen entails administration once per week, once every two weeks, once every three weeks, once every four weeks, once a month, once every 3 months or once every three to 6 months. Preferred dosage regimens for the drug combination of the invention include 1 mg/kg body weight or 3 mg/kg body weight via intravenous administration, with the drugs each being given simultaneously using one of the following dosing schedules; (i) every four weeks for six dosages, then every three months; (ii) every three weeks; (iii) 3 mg/kg body weight once followed by 1 mg/kg body weight every three weeks. In some methods, dosage is adjusted to achieve a plasma fusion protein concentration of about 1-1,000 ug/ml and in some methods about 25-300 ug/ml.

In embodiments, a subject is treated using a dosing regimen that includes SIRPαFc drug of SEQ ID NO:8 or SEQ ID NO:9 at 0.1 mg/kg weekly (or 0.2 mg/kg weekly, or 0.3 mg/kg weekly) and niraparib at about 3 mg/kg every 2 weeks. The SIRPαFc protein displays negligible binding to red blood cells. There is accordingly no need to account for an RBC "sink" when dosing with the drug combination. Relative to other CD47 blocking agents that are bound by RBCs, it is estimated that the present SIRPαFc fusion can be effective at doses that are less than half the doses required for drugs that become RBC-bound, such as CD47 antibodies. Moreover, the SIRPα-Fc fusion protein is a dedicated antagonist of the SIRPα-mediated signal, as it displays negligible CD47 agonism when binding thereto. There is accordingly no need, when establishing medically useful unit dosing regimens, to account for any stimulation induced by the drug.

Each drug in the combination can also be administered as a sustained release formulation, in which case less frequent administration is required. Dosage and frequency vary depending on the half-life of the fusion protein and other agents in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient show partial or complete amelioration of symptoms of disease. Thereafter, the patient can be treated using a prophylactic regimen.

The present treatment also includes the use of CD47 blockade with PARP inhibition as described above and further including radiation therapy, known also as radiotherapy or RT. In an embodiment, the RT is external beam radiotherapy (EBR). In an alternative embodiment, the RT is brachytherapy. The main function of radiotherapy is to produce DNA strand breaks, causing severe DNA damage and leading to cell death. Combining radiation therapy with PARP inhibitors can lead to formation of double strand breaks from the single-strand breaks generated by the radiotherapy, especially but not only in tumor tissue with BRCA1/BRCA2 mutations. The BRCA genes (breast cancer antigen genes) BRCA1 and BRCA2 encode unrelated proteins, but both are expressed in breast and other tissue, where they help repair damaged DNA, or destroy cells if DNA cannot be repaired. They are involved in the repair of chromosomal damage with an important role in the error-free repair of DNA double-strand breaks. If BRCA1 or BRCA2 is damaged by mutation, the DNA is not repaired and the risk for breast cancer increases BRCA1 and BRCA2 have been described as "breast cancer susceptibility genes" and "breast cancer susceptibility proteins.

Radiotherapy is the treatment of cancer and other diseases with ionizing radiation. It is a very well established approach to the treatment of numerous types of cancer, and has been refined so that each cancer type typically receives an RT treatment regimen tailored for that particular cancer. Ionizing radiation deposits energy that injures or destroys cells in the area being treated by damaging their genetic material, making it impossible for these cells to continue to grow. A combination therapy that comprises radiotherapy can be used to treat localized solid tumors, such as cancers of the ovary, prostate, skin, tongue, larynx, brain, breast, or cervix. It can also be used to treat so-called blood cancers including leukemia and lymphoma (cancers of the blood-forming cells and lymphatic system, respectively).

In an embodiment, the RT is external-beam radiation (EBR) therapy. Conventional external beam radiation therapy (2DXRT) is delivered via two-dimensional beams using kilovoltage therapy X-ray units or medical linear accelerators which generate high energy x-rays. 2DXRT mainly consists of a single beam of radiation delivered to the patient from several directions: often front or back, and both sides. External-beam radiation therapy is most often delivered in the form of photon beams (either x-rays or gamma rays). Many types of external-beam radiation therapy are delivered using a linear accelerator that uses electricity to form a stream of fast-moving subatomic particles. Subjects can receive external-beam radiation therapy in daily treatment sessions over the course of several weeks. The number of treatment sessions depends on many factors, including the total radiation dose that will be given. Another useful type of external-beam radiation therapy is 3-dimensional conformal radiation therapy (3D-CRT). 3D-CRT uses sophisticated computer software and advanced treatment machines to deliver radiation to very precisely shaped target areas.

Still other methods of external-beam radiation therapy are useful in the present treatment method. These include intensity-modulated radiation therapy (IMRT), which uses hundreds of tiny radiation beam-shaping devices, i.e., collimators, to deliver a dose of radiation. The collimators can be stationary or can move during treatment, allowing the intensity of the radiation beams to change during treatment sessions, so that different areas of a tumor or nearby tissues can be hit with different doses of radiation. IMRT can be used to increase the radiation dose to treatment areas.

In use, each of the three treatment modalities in the present treatment combination can be utilized as it would be used in monotherapy, i.e., as it would be used independently of its combination with any other agent. Methods of administration and dosing will be consistent with established applications as a monotherapeutic, so that each modality provides an anti-cancer benefit that will be enhanced when the modalities are combined in treating a given subject. The combination of radiation, PARPi and SIRPαFc would be administered in cases where radiation was considered as the primary modality. In those cases where radiation is not a treatment option, then treatment can consist of the PARPi+SIRPαFc combination therapy only.

In treatment combination, the PARPi would be administered prior to radiotherapy, while SIRPαFc would be administered concurrently therewith.

In embodiments, subjects will receive most types of external-beam radiation therapy up to 5 days a week for several weeks. One dose (a single fraction) of the total planned dose of radiation is given each day. Occasionally, two treatments a day are given. Most types of external-beam radiation therapy are given in once-daily fractions, so that damage to normal tissue is minimized and to increase the likelihood that cancer cells are exposed to radiation at the points in the cell cycle when they are most vulnerable to DNA damage. Fractionation of a dosing schedule is now common, including accelerated fractionation where treatment is given in larger daily or weekly doses to reduce the number of weeks of treatment; hyperfractionation whereby smaller doses of radiation are given more than once a day; and hypofractionation by which larger doses are given once a day or less often to reduce the number of treatments.

Fractionation regimens are individualised between different radiation therapy centers and even between individual doctors. In North America, Australia, and Europe, the typical fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used near the end of a course of treatment. This schedule, known as a concomitant boost regimen or hyperfractionation, is used on tumors that regenerate more quickly when they are smaller. In particular, tumors in the head-and-neck demonstrate this behavior.

Hypofractionation is a radiation treatment in which the total dose of radiation is divided into large doses. Typical doses vary significantly by cancer type, from 2.2 Gy/fraction to 20 Gy/fraction. The logic behind hypofractionation is to lessen the possibility of the cancer returning by not giving the cells enough time to reproduce and also to exploit the unique biological radiation sensitivity of some tumors. One commonly treated site where there is very good evidence for such treatment is in breast cancer. Short course hypofractionated treatments over 3-4 weeks e.g. 40 Gy in 15 fractions or 42.5 Gy in 16 fractions, have been shown to be as effective as more protracted 5-6 week treatments with respect to cancer control.

An alternative fractionation schedule is Continuous Hyperfractionated Accelerated Radiation therapy. CHART is used to treat lung cancer and consists of three smaller fractions per day. Another increasingly well-known alternative fractionation schedule, used to treat breast cancer, is called Accelerated Partial Breast Irradiation (APBI). APBI can be performed with external beam radiation. APBI involves two high-dose fractions per day for five days, compared to whole breast irradiation, in which a single, smaller fraction is given five times a week over a six-to-seven-week period.

Thus, for radiotherapy, dosing levels and regimens will be determined by the type, location and stage of cancer being treated. The dose can be photon- or proton-based and expressed either in Roentgens or in Gray units, to indicate the exposed dose (Rn) or the absorbed dose (Gy) of radiation. The Gray is a derived unit of ionizing radiation dose, which is a measure of the amount of radiation energy absorbed by 1 kilogram of human tissue. It is related to the rad, which is 0.01Gy. Generally, appropriate dosing will range from about 1 to about 300 Gy per exposure. Total dosages per exposure can vary from about 1 to about 500 Gy and particularly 40-70Gy.

By definition, one roentgen of air kerma (kinetic energy released per unit mass) deposits 0.00877 grays (0.877 rads) of absorbed dose in dry air, or 0.0096 Gy (0.96 rad) in soft tissue. One roentgen (air kerma) of X-rays may deposit anywhere from 0.01 to 0.04 Gy (1.0 to 4.0 rad) in bone depending on the beam energy. Dosage ranges for X-rays in the present method range from daily doses of 50 to 200 roentgens as well as all intermediate dosage levels therebetween for prolonged periods of time such as 3 to 4 weeks, to single doses of 2000 to 6000 roentgens (including, but not limited to 2500, 3000, 3500, 4000, 4500, 5000, and 5500 roentgens).

External beam radiotherapy schedules used in accordance with the present method can also vary. In certain embodiments, a particular schedule can comprise daily treatments about 5 times per week for about six to about seven weeks or can comprise about twice daily treatments for about two to about three weeks.

In alternative embodiments, the radiation therapy can be brachytherapy. In brachytherapy, a source of radiation source is placed inside or next to the area requiring treatment. It is used as a treatment particularly for breast, cervical, prostate and skin cancer. Brachytherapy involves the precise placement of short-range radiation-sources (radioisotopes) directly at the tumour. These are enclosed in a protective capsule or wire, which allows the ionizing radiation to treat and kill surrounding tissue.

A course of brachytherapy thus begins with placement of the radiation source and ends with its removal or when the source radiation expires. The dose rate of brachytherapy refers to the level or 'intensity' with which the radiation is delivered to the surrounding medium and is expressed in Grays per hour (Gy/h). Low-dose rate (LDR) brachytherapy involves implanting radiation sources that emit radiation at a rate of up to 2 Gy/h. LDR brachytherapy is commonly used for cancers of the oral cavity, oropharynx, sarcomas and prostate. Medium-dose rate (MDR) brachytherapy is characterized by a medium rate of dose delivery, ranging between 2 Gy/h to 12 Gy/h. In high-dose rate (HDR) brachytherapy, the rate of dose delivery exceeds 12 Gy/h. The most common applications of HDR brachytherapy are in tumours of the cervix, esophagus, lungs, breasts and prostate.

Pulsed-dose rate (PDR) brachytherapy involves short pulses of radiation, typically once an hour, to simulate the overall rate and effectiveness of LDR treatment. Typical tumour sites treated by PDR brachytherapy are gynaecological and head and neck cancers.

The placement of radiation sources in the target area can be temporary or permanent. Temporary brachytherapy involves placement of radiation sources for a set duration (usually a number of minutes or hours) before being withdrawn. Treatment duration will depend on many factors, such as the required rate of dose delivery and the type, size and location of the cancer. In LDR and PDR brachytherapy, the source stays in place up to 24 hours and is then removed, while in HDR brachytherapy this time is typically just a few minutes.

Permanent brachytherapy, also known as seed implantation, involves placing small LDR radioactive seeds or pellets (about the size of a grain of rice) in the tumour or treatment site and leaving them there permanently to gradually decay. Over a period of weeks or months, the radiation emitted by the sources will decline to almost zero. The inactive seeds then remain in the treatment site but with no lasting effect.

Commonly used sources of brachytherapy radiation include Cesium-131, Cesium-137, Cobalt-60, Iridium-192, Iodine-125, Palladium-103, Ruthenium-106 and Radium-226.

As noted, in the present treatment method, the CD47 blocking agent, such as a CD47-binding form of human SIRPα, is used in combination with a PARP inhibitor. In the alternative, the CD47 blocking agent is used in combination with both radiation therapy and PARP inhibition. These methods are useful to treat CD47+ diseases and particularly hyperproliferative disease and especially cancer. In terms of an anti-cancer effect, such as a depletion of CD47+ cancer cells, the treatment modalities cooperate to provide an enhanced reduction in cancer cell vitality, activity or mortality. The cooperative or enhanced effect of the combination is also revealed in the context of other parameters, such as a reduction in cancer cell viability, size, number, or distribution, or improvement in overall burden of a tumour.

The treatment modalities in the present combination can be delivered sequentially or, essentially at the same time. In embodiments, the RT can be given before administration of SIRPαFc. In general, the delivery of one modality relative to the other in temporal terms refers to the delivery of one modality in terms of one course of treatment, versus the delivery of the other modality in terms of its course of treatment. Thus, concurrent delivery means that courses of treatment overlap, whereas successive or consecutive or sequential delivery means that courses of treatment have starting points that do not overlap.

In some embodiments, EBR therapy can be administered within about 1-60 minutes, or 2-48 hours or more prior to and/or after administering the CD47 blocking agent. In other embodiments, radiation therapy can be administered within from about 1 day to about 21 days prior to and/or after administering the CD47 blocking agent. In some embodiments, the time period for treatment can be extended significantly, however, where several weeks (e.g., about 1, about 2, about 3, about 4, about 5, about 6, about 7, or about 8 weeks or more) lapse between the administration of the CD47 blocking agent and the radiation therapy. It is important only that the effect of one agent is present in the subject when the other agent is administered. It is desirable in one embodiment that the agents are used concurrently and that their activities overlap actively within the subject undergoing treatment. In the context of brachytherapy, the modalities can be used concurrently, meaning that internal radiation is in place during a course of treatment with the CD47-blocking agent and PARPi, or the CD47-binding agent and PARPi treatment can be administered to a subject that has completed a course of brachytherapy.

It will be appreciated that the present methods can also be used to treat all subjects who could benefit from the present method including mammals including humans. The present treatment combination is also useful to treat a variety of disease cells. These include particularly CD47+ cancer cells, including liquid and solid tumours. Solid tumours can be treated with the present drug combination, to reduce the size, number or growth rate thereof and to control growth of cancer stem cells. The present therapy is also helpful to extend survival such as overall survival. Such solid tumours include CD47+ genito-urinary tumours and others such as in bladder, brain, head and neck, breast, lung, colon, ovary, fallopian peritoneal, prostate, gastric tissue, colon, liver, pancreas, endometrium, Ewing's sarcoma, skin and other tissues as well. In one embodiment, the drug combination can used to inhibit the growth or proliferation of hematological cancers. As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma, Sezary Syndrome and mycosis fungoides.

In some embodiments, the hematological cancer treated with the treatment combination is a CD47+ leukemia, preferably selected from acute lymphocytic leukemia, acute myeloid leukemia, chronic lymphocytic leukemia, chronic myelogenous leukemia, and myelodysplastic syndrome, preferably, human acute myeloid leukemia.

In other embodiments, the hematological cancer treated with the SIRPαFc protein is a CD47+ lymphoma or myeloma selected from Hodgkin's lymphoma, both indolent and aggressive non-Hodgkin's lymphoma, Burkitt's lymphoma, follicular lymphoma (small cell and large cell), multiple myeloma (MM), cutaneous T cell lymphoma, giant cell myeloma, heavy-chain myeloma, and light chain or Bence-Jones myeloma as well as leimyosarcoma.

In other embodiments, the cancer treated with the treatment combination is a glioma or glioblastoma. In a further embodiment the treated cancer is melanoma.

In particular embodiments, the present combination can be used to treat germline mutated e.g., BRCA1, BRCA2, IDH or PALB2 mutated, advanced ovarian cancer, breast cancer, advanced prostate cancer, and colorectal cancer especially when the PARPi is oliparib or rucaparib; and epithelial ovarian, fallopian tube, and primary peritoneal cancer especially when the PARPi is niraparib; and advanced hematological malignancies and for advanced or recurrent solid tumors and for metastatic germline BRCA mutated breast cancer, especially when the PARPi is talazoparib; and for metastatic melanoma, advanced ovarian cancer, triple-negative breast cancer and non-small cell lung cancer especially when the PARPi is veliparib.

More particularly, the types of ovarian cancer that can be treated with the present treatment combinations include those within the three major categories, according to the kind of cells from which they were formed, i.e., (1) epithelial tumors that arise from cells that line or cover the ovaries; (2) germ cell tumors that originate from cells that are destined to form eggs within the ovaries; and (3) sex cord-stromal cell tumors that begin in the connective cells that hold the ovaries together and produce female hormones. Also included are tumors that are adjacent to ovarian tissues, such as extraovarian peritoneal carcinoma (intraperitoneal carcinomatosis).

The common epithelial tumors begin in the surface epithelium of the ovaries and account for about 90% of all ovarian cancers. They are divided into a number of subtypes—including serous, endometrioid, mucinous, and clear cell tumors—that can be further classified as benign (noncancerous) or malignant (cancerous) tumors. Serous tumors are the most widespread forms of ovarian cancer. They account for 40% of common epithelial tumors. About 50% of these tumors are malignant, 33% are benign, and 17% are of borderline malignancy. Endometrioid tumors represent approximately 20% of common epithelial tumors. In about 20% of individuals, these cancers are associated with endometrial carcinoma (cancer of the womb lining). In 5% of cases, they also are linked with endometriosis, an abnormal occurrence of endometrium (womb lining tissue) within the pelvic cavity. The majority (about 80%) of these tumors are malignant, and the remainder (roughly 20%) usually are of borderline malignancy. Mucinous tumors make up about 1% of all common epithelial tumors. Most (approximately 80%) of these tumors are benign, 15% are of borderline malignancy, and only 5% are malignant. Clear cell tumors account for about 6% of common epithelial tumors. Nearly all of these tumors are malignant. Approximately one-half of all clear cell tumors are associated with endometriosis. Also treatable with the present combinations are the rare types of ovarian tumours, such as Brenner tumors, undifferentiated tumors, and transitional cell tumors as well as germ cell tumours that are formed from egg-making cells within the ovaries.

In a specific embodiment, the subject receiving treatment is afflicted with ovarian cancer, and the treatment comprises 0.1-0.3 mg/kg weekly of a SIRPαFc drug comprising SEQ ID NO:8 or SEQ ID NO:9, in combination with niraparib at 100-300 mg peroral (or 5-50 mg/kg) daily for 2 weeks. In a further embodiment, the subject receiving this combination also receives radiation therapy.

In another aspect, there is provided a kit useful to perform the present method, comprising at least one of a PARP inhibitor and a CD47 blocking agent in a container and suitably bearing a label. Suitable containers include, for example, bottles, vials, syringes, and test tubes. The containers may be formed from a variety of materials such as glass or plastic. The container holds a composition which is effective in combination for treating the disease and may have a sterile access port (for example the container may be an intraveneous solution bag or vial having a stopper pierceable by a hypodermic injection needle). The label on or associated with, the container indicates that the composition is used for treating a cancer condition. The article of manufacture may further compromise a second container compromising a pharmaceutically-acceptable buffer, such as phosphate-buffered saline, Ringer's solution and dextrose solution. It may further include the other of the two components useful in the present combination therapy, e.g., a PARP inhibitor in the case whether the first container comprises a CD47 blocking agent. The kit may further comprise, other matters desirable from a commercial and use standpoint, including other buffers, diluents, filters, needles, syringes, and package inserts with instructions for use in accordance with the present treatment method. Control agents or standards useful in the method can also be included in the kit, such as a preparation standard, calibrator or control.

Examples

The combination of RT, a PARP inhibitor and a CD47-blocking agent SIRPαFc was examined in xenograft tumor models.

Materials and Methods

The in vivo efficacy of SIRPαFc, RT and niraparib (a PARP inhibitor) was evaluated alone or in combination in intraperitoneal tumor xenografts of BRCA competent and knock-down luciferase-expressing ovarian cancer cells in NOD/SCID mice. SIRPαFc (10 mg/kg) was administered intraperitoneally 1 hour prior to RT, 3 times per week for 3 weeks. Niraparib (50 mg/kg) was administered 1 hour prior to RT, 5 times per week for 1 week. Mice were treated with whole abdomen radiotherapy (external beam radiation therapy) at a dose of 2 Gy for 2 fractions using an image-guided small animal irradiator (225 kVp, 13 mA). Treatment was initiated on day 7 following tumor inoculation. Treatment efficacy was assessed by bioluminescent imaging (BLI) and animal survival. Systemic toxicity was evaluated by clinical parameter scoring.

Results

While SIRPαFc monotherapy inhibited tumor growth in the BRCA competent xenograft model, the combination of SIRPαFc and RT significantly improved survival compared to RT alone, with the median survival prolonged from 34 days to 47 days (p=0.0085).

Mice bearing BRCA knock-down tumors had improved survival with the SIRPαFc+ niraparib combination compared to vehicle control (median survival 41 days vs. 42 days, p=0.013). SIRPαFc significantly enhanced survival when combined with radiotherapy, (median survival 42.5 days, RT alone, vs. 46.5 days, SIRPαFc+RT, p=0.0009) with extended survival observed in the RT+SIRPαFc+ niraparib group (median survival 52 days, p=0.004).

Standard treatment for ovarian cancer—cytoreductive surgical debulking followed by chemotherapy demonstrates a high relapse rate of 70%, and PARPi are approved to be used in patients with recurrent advanced ovarian cancer who have received one or more prior chemotherapy regimens.

Recent advancements in RT facilitates the delivery of precise and conformal radiation doses to tumor, with minimal exposure of healthy tissues to RT and therefore an acceptable level of toxicity. As such, RT has gained interest in the treatment ovarian cancer. The fact that PARP inhibitors function as effective radiosensitizers further makes the combination of PARP inhibitors+RT a treatment strategy with great potential.

However, PARPi as a monotherapy is associated with risk of severe hematologic toxicities, which usually leads to dose delays and interruptions similar to cytotoxic chemotherapeutic agents, and novel treatment strategy is highly needed. In the present study, it is demonstrated that SIRPαFc is able to enhance the efficacy of PARPi (niraparib) and/or RT without showing additional toxicity.

The current study provides supportive evidence for combining innate modulation (SIRPαFc) with radiation therapy to improve overall survival in patients with ovarian cancer. Additionally, patients with BRCA mutated tumors can benefit from triple therapy with SIRPαFc, niraparib and RT. The combination of SIRPαFc with PARPi and/or RT may be used to lower to the effective dose of PARPi and further to minimize the toxicities associated with the treatment.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method for treating a subject presenting with CD47+ disease cells, comprising administering to the subject a PARP inhibitor and a CD47 blocking agent in combination with radiation therapy, wherein the CD47 blocking agent is a CD47-binding SIRPα polypeptide and wherein the CD47-binding SIRPα polypeptide is an Fc fusion protein comprising a CD47-binding region of soluble human SIRPα.

2. The method according to claim 1, wherein the PARP inhibitor is an inhibitor of PARP-1.

3. The method according to claim 1, wherein the PARP inhibitor is talazoparib, veliparib, niraparib, olaparib, rucaparib, or iniparib.

4. The method according to claim 1, wherein the Fc fusion protein comprises SEQ ID NO: 8.

5. The method according to claim 1, wherein the Fc fusion protein comprises SEQ ID NO: 9.

6. The method according to claim 1, wherein the Fc fusion protein comprises soluble SIRPα having one or more activity-enhancing amino acid substitutions selected from $L^4V/I$, $V^6I/L$, $A^{21}V$, $V^{27}I/L$, $I^{31}T/S/F$, $E^{47}V/L$, $K^{53}R$, $E^{54}Q$, $H^{56}P/R$, $S^{66}T/G$, $K^{68}R$, $V^{92}I$, $F^{94}V/L$, $V^{63}I$, and $F^{103}V$.

7. The method according to claim 1, wherein the radiation therapy is external beam radiation therapy.

8. The method according to claim 1, wherein the CD47+ disease cells are CD47+ cancer cells.

9. The method according to claim 8, wherein the CD47+ cancer cells are blood cancers or solid tumours.

10. The method according to claim 8, wherein the cancer cells are cells of a cancer type selected from acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome.

11. The method according to claim 8 wherein the cancer is a lymphoma selected from a non-Hodgkin's lymphoma, both indolent and aggressive non-Hodgkin's lymphoma, T cell lymphoma, CD20+ lymphoma, Burkitt's lymphoma, and small cell follicular lymphoma, and large cell follicular lymphoma.

12. The method according to claim 8, wherein the cancer is a myeloma selected from multiple myeloma (MM), giant cell myeloma, heavy-chain myeloma, and light chain or Bence-Jones myeloma.

13. The method according to claim 8, wherein the cancer is melanoma, ovarian cancer, CTCL, mycosis fungoides, breast cancer, or glioblastoma.

* * * * *